(12) United States Patent
De Santis et al.

(10) Patent No.: US 8,562,947 B2
(45) Date of Patent: Oct. 22, 2013

(54) OXIDIZED AVIDIN WITH HIGH RESIDENCY TIME IN THE TREATED TISSUES

(75) Inventors: Rita De Santis, Pomezia (IT); Carlo Antonio Nuzzolo, Rome (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 532 days.

(21) Appl. No.: 12/670,925

(22) PCT Filed: Jul. 16, 2008

(86) PCT No.: PCT/EP2008/059260
§ 371 (c)(1),
(2), (4) Date: Feb. 24, 2010

(87) PCT Pub. No.: WO2009/016031
PCT Pub. Date: Feb. 5, 2009

(65) Prior Publication Data
US 2010/0239497 A1   Sep. 23, 2010

(30) Foreign Application Priority Data

Aug. 2, 2007 (EP) .................... 07113733
Jun. 3, 2008 (EP) .................... 08157473

(51) Int. Cl.
*A61K 51/04* (2006.01)
*C07K 17/10* (2006.01)
(52) U.S. Cl.
USPC ........................................ 424/1.69; 530/367
(58) Field of Classification Search
None
See application file for complete search history.

(56) References Cited

U.S. PATENT DOCUMENTS

| | | | |
|---|---|---|---|
| 5,716,594 A * | 2/1998 | Elmaleh et al. | 424/1.41 |
| 2002/0137125 A1* | 9/2002 | Zhu | 435/68.1 |
| 2004/0101901 A1* | 5/2004 | Tabaczewski | 435/7.1 |
| 2004/0191832 A1 | 9/2004 | Wilchek et al. | |
| 2007/0092531 A1* | 4/2007 | McKenzie et al. | 424/185.1 |

FOREIGN PATENT DOCUMENTS

WO   2004/093916   11/2004

OTHER PUBLICATIONS

Bruch RC, White HB 3rd. Compositional and structural heterogeneity of avidin glycopeptides. 1982 Biochemistry 21: 5334-5341.*
Yao Z, Zhang M, Sakahara H, Saga T, Arano Y, Konishi J. Avidin targeting of intraperitoneal tumor xenografts. 1998 J. Natl. Cancer Inst. 90: 25-29.*
Green, N., "Avdin. 3. the Nature of the Biotin-Binding Site" The Biochemical Journal, vol. 89, Dec. 1963, pp. 599-609.

* cited by examiner

*Primary Examiner* — Michael G Hartley
*Assistant Examiner* — Jennifer Lamberski
(74) *Attorney, Agent, or Firm* — Lucas & Mercanti, LLP

(57) ABSTRACT

The present invention describes chemically modified avidins that have higher permanence in treated tissues compared to wild type avidin. Avidin oxidation is performed by periodate incubation in the presence of the low affinity ligand HABA which, occupying the biotin binding sites, prevents protein denaturation during the oxidation step. Periodate oxidation generates CHO groups from avidin mannose ring opening that, once injected, react with tissue $NH_2$ residues to form stable Schiff's bases. The anchored avidins maintain the ability to bind biotinylated agents endowed of therapeutic activity, like radiolabeled biotins, stem cells and somatic cells, useful for brachytherapies like Intraoperative Avidination Radionuclide Therapy (IART®) or degenerative or genetic diseases.

6 Claims, 11 Drawing Sheets

UV spectra of absorbance of WTavidin, OXavidin and OXavidin$_{HABA}$

SEC HPLC analysis of OXavidin$_{HABA}$ compared to OXavidin and WTavidin

Figure 3
Tissue permanence of $^{125}$I-avidins after i.m. injection
Figure 3a
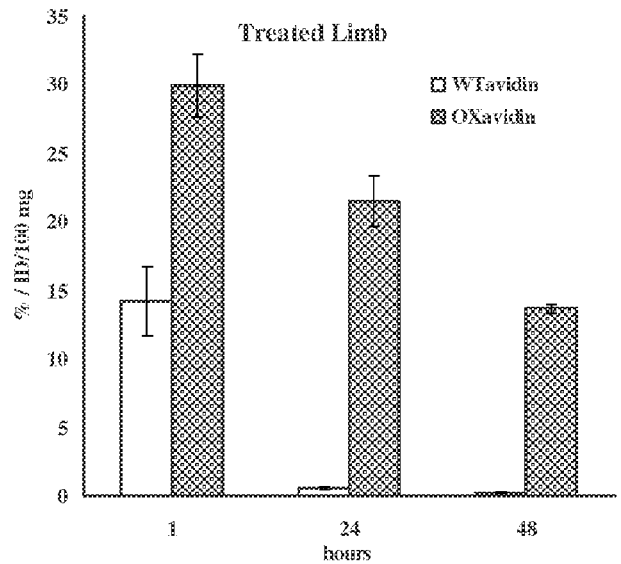
Figure 3b
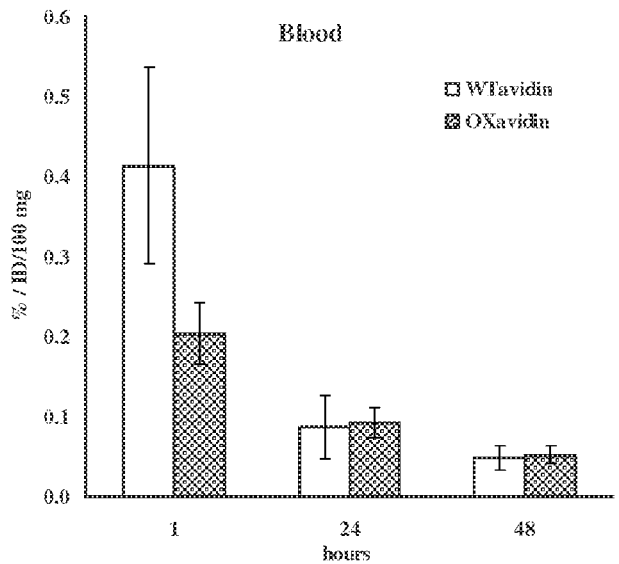

Long term permanence of Oxavidin$_{HABA}$ compared to WTavidin in a treated tissue Tissue permanence of OXavidin$_{HABA}$ compared to WTavidin and PEGavidin Immunofluorescence of WTavidin or OXavidin$_{HABA}$ in treated tissue 24 hours after injection Tissue permanence of $^{111}$InST2210 i.v. injected 48 hours after tissue avidination a b d                                                   e

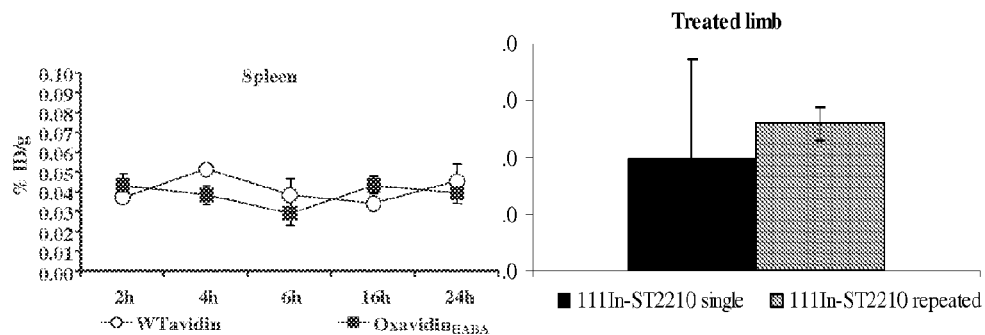
Figure 8
Tissue permanence of the complex Oxavidin$_{HABA}$/ST2210 compared to WTavidin/ST2210
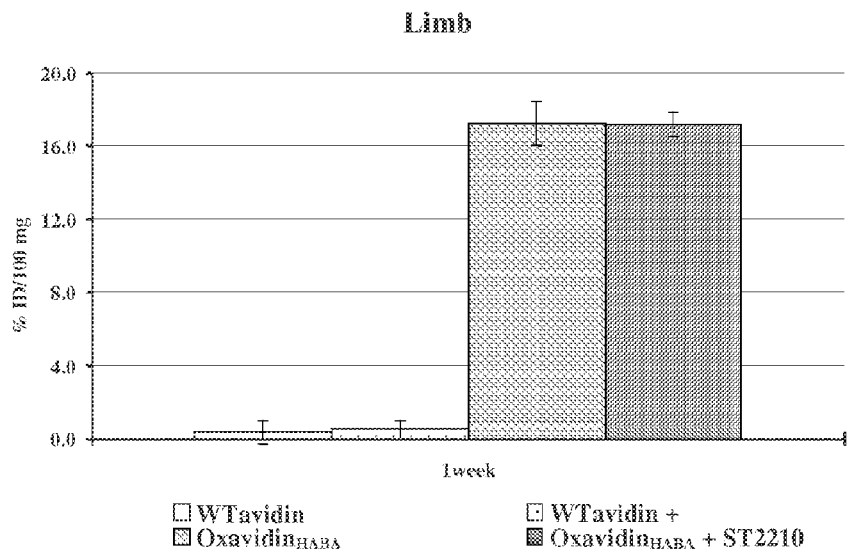

Brain permanence of OXavidin$_{HABA}$ compared to WTavidin

OXIDIZED AVIDIN WITH HIGH RESIDENCY TIME IN THE TREATED TISSUES

This application is a 35 U.S.C. §371 national phase of PCT/EP2008/059260 filed on Jul. 16, 2008, which claims priority to and the benefit of European Application No. 08157473.3 filed on Jun. 3, 2008 and European Application No. 07113733.5 filed on Aug. 2, 2007, the contents of which are incorporated herein by reference.

FIELD OF THE INVENTION

The invention described herein relates to modified avidins useful to bind biotinylated compounds or cells and maintain them into a site needing therapy.

BACKGROUND OF THE INVENTION

The avidin-biotin system has been known for many years as an exceptional tool for qualitative and quantitative studies in interactions between small molecules and biological receptors (Wilchek, M., et al., *Immunol. Today*, 1984, 6, 39).

Avidin is a glycoprotein of about 68 kDa present in the egg white and showing high affinity for the vitamin H biotin. Its dissociation constant ($K_d \sim 10^{-15}$M) is the lowest known in nature (Green N. M., et al., *Biochem. J.*, 1970, 118, 67; Green, N. M., *Adv. Protein Chem.*, 1975, 29, 85). It is composed of four subunits of identical amino acid sequence, each of which can potentially bind one molecule of biotin. Glycosylation accounts for about 10% of its molecular weight with an average of four to five mannose and three N-acetylglucosamine residues per subunit (Bruch R. C., et al., *Biochemistry*, 1982, 21, 5334).

In 1988, a study regarding interaction between radiolabelled biotin derivatives and avidin was reported (Garlick R. K., et al., *J. Biol. Chem.*, 1988, 263, 210).

In WO04093916 in the name of the Applicant, a two-step perioperative therapy of solid tumours was described as a novel form of brachytherapy. The first step involved the administration within the operated area of a biotinylated specific antibody followed by injection of native or PEG-ylated avidin in order to construct an "artificial receptor". Then, within the second step, the proper anticancer agent coupled to biotin was administered systemically. The second step needed to be performed within 4 to 72 hours from the surgical removal of the tumour. However, no suggestions of direct avidination through covalent binding of avidin to the considered tissue were provided.

Clinical applications of this two-step brachytherapy using avidin in the first step and radiolabelled biotin-DOTA (ST2210) in the second step, proved to be effective in delivering partial irradiation to the surgically operated area in breast cancer patients (Paganelli G., et al., *The Breast*, 2007, 16, 17; Paganelli G., et al., *Clin. Canc. Res.*, 2007, 13, 5646). The radiation dose released to the surgically operated index quadrant, in 11 patients, was an average of 20 Gy for an administered dose of 100 mCi. This boost represents about ⅓ of the expected 60 Gy delivered to this type of patients by the current standard External Beam Radiotherapy (EBR).

The uses of streptavidin antibody constructs with biotin-radionuclide conjugates in the treatment of patients with malignant gliomas, and of bispecific antibodies with hapten-radionuclides in the therapy of tumours expressing carcino-embryonic antigen were reported recently (Goldenberg, D. M., et al., *J. Clin. Oncol.*, 2006, 24, 823). However, in quite a few cases renal toxicity appeared due to the too elevated dose that passed the kidney.

One of the main problems when treating with avidin, resides in its rapid clearance from the body. Lately, research efforts focussed at finding "modified avidin" with a longer half-life. One such approach consisting in linking the protein via free amino groups to monomethoxypolyethylene glycol, resulted in prolonged plasma half-life of the modified avidin with 8% of the i.v. injected dose still present in the tumour after 5 hours and 6% after 72 hours when avidin was coupled to PEG-20 kDa (Caliceti P., et al., *J. Control. Release*, 2002, 83, 97).

A pharmacokinetic study demonstrating the influence of the size of the PEG moiety highlighted the fact that the heavier the PEG unit the shorter the half-life, meanwhile biotin-avidin affinity degree was following an opposite trend (Salmaso S., et al., *Biochim. Phys. Acta*, 2005, 1726, 57).

Another pharmacokinetic and biotin-binding properties study on different PEG-ylated avidin showed that 7 PEG moieties per avidin protein was the best ratio, allowing increasing the plasma half-life and reducing the immunogenecity of avidin. However, no details were given in animal model with regard to biotinylated drug accumulation within tumours (Chinol M., et al., *Br. J. Cancer*, 1998, 78, 2, 189).

As an alternative to PEG-avidin, thermoresponsive polymers have been investigated. Poly(N-isopropylacrylamide-co-acrylamide)-avidin showed higher residence time in bloodstream compared to avidin and lower accumulation within the liver (Salmaso S., et al., *Int. J. Pharm.*, 2007, 340, 20). However, also in this case no details in animal model with regard to biotinylated drug accumulation within tumours were reported.

Unfortunately, up to now, no efficient and selective method to specifically localize therapeutic agents is available.

Therefore, improvement of anticancer therapy is still a great need and a major area of efforts for pharmaceutical companies.

Avidin-biotin binding interaction is dependent on the protein portion. In fact, deglycosylated avidin preserves the biotin binding capacity (Hiller Y., et al, *Biochem. J.*, 1987, 248, 167; Rosebrough S. F., et al., *J. Nucl. Med.*, 1996, 37, 8, 1380).

Increased accumulation and permanence of a therapeutic agent within the area to be treated could be achieved through the avidination of the tissue with a modified avidin endowed with a higher tissue permanence compared to wild type avidin.

Such a strategy would avoid the need of systemic administration of avidin and consequently prevent any side effects related to such therapy. In addition, an increased avidination of the relevant tissue would result in a less toxic treatment due to lower distribution of the anticancer agent in non relevant organs and reduced dose of anticancer agent to obtain the same effect as with the wild type avidin.

It has now been found that by oxidizing the glycosylated part of avidin, stable avidination of surrounding tumour tissue can be obtained, allowing a biotinylated anticancer agent to better concentrate in such region.

DESCRIPTION OF THE INVENTION

The present invention involves a chemically oxidized avidin able to interact with tissues in vivo, through a reversible covalent chemical bond, in a way that delays its diffusion. Such oxidized avidin is administered during the surgical step or by injecting a selected organ or tissue needing therapy.

Oxidation of avidin by means of 10 mM of sodium periodate was reported lately (US20020137125). In the latter, the authors coupled the oxidized avidin with phosphopentamannose-hydrazine to obtain an imine derivative highly phosphorylated that could then be administered to the patient for modifying lysosomal enzyme, this enhancing the efficacy of enzyme replacement therapy of lysosomal diseases. It is noteworthy that the imine formation does not intervene in vivo. It has also to be noted that no activity of such modified avidin is reported in that application.

In particular, the present invention refers to an oxidized avidin, obtained by oxidation of the sugar moieties of the glycoprotein, exhibiting higher permanence in tissues compared to wild type avidin (WTavidin) meanwhile minimizing the side-effects encountered when using previously reported modified avidin proteins.

Tissue binding of oxidized avidin is highly homogenous and does not depend as in IART on the ability of positively charged avidin to localise in tumour and inflammatory tissues. Therefore, oxidized avidin action is not limited to the specific interaction with tumour cells thus allowing avidination of the tissues surrounding the surgically removed tumours that are known to contain spare tumour cells not easily accessible to direct targeting with wild type avidin.

A first embodiment of the present invention refers to a chemically modified wild type avidin by means of oxidative ring opening of the pyranosidic sugar, thus generating aldehyde moieties that interact with amino residues present in the tissue of concerns.

CHO groups, at acidic pH (below 6.0), are substantially inert against proteins $NH_2$ because the protonated $NH_3^+$ form is present. However at pH≥7, CHO groups react with protein $NH_2$ residues to form Schiff's bases. An example of the chemical oxidation of a representative mannose residue of wild type avidin and the following reaction of the new-formed CHO groups with the amino groups (R—$NH_2$, where R is a tissue protein residue) is given in Scheme 1.

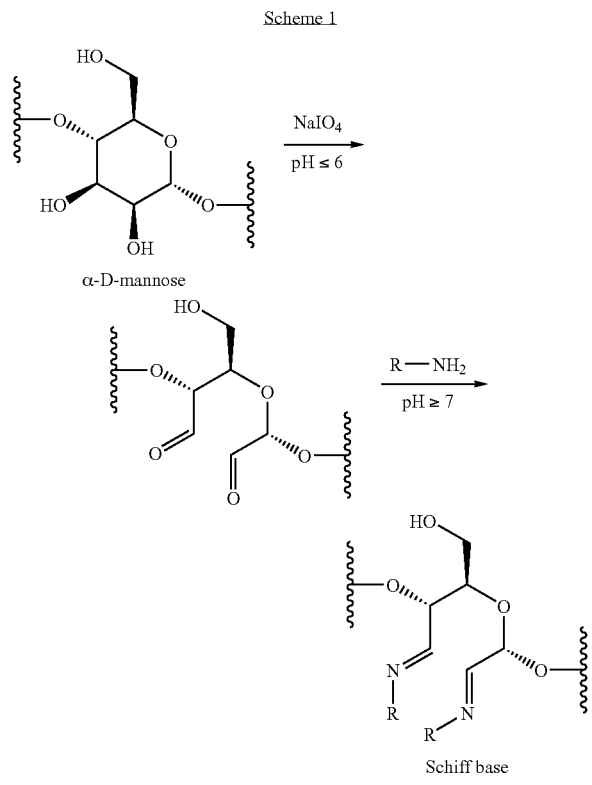

Scheme 1

This sugar oxidation is achieved according to the well-known method based on reaction of the native avidin with sodium periodate (Zaborsky, O. R., et al., *Biochem. Bioph. Res. Comm.*, 1974, 61, 1, 210; Green, N. M., Biochem. J., 1963, 89, 599).

Avidin oxidation however, is known to result in damage to some protein amino-acidic residues, i.e. oxidation of tryptophan that is involved in the biotin-binding site, causing a lower affinity towards biotin and/or biotin derivatives (US20040191832; Green, N. M., *Biochem. J.*, 1963, 89, 599).

It has now been found that binding of avidin to the low affinity ligand 4-hydroxyazobenzene-2'-carboxylic acid (HABA), prior to the oxidation step, confers to the former a conformation that prevents oxidation of the tryptophan residues as revealed by UV spectra analysis of such derivatives. The lowering of the characteristic inflexions at 282 and 291 nm, in the UV spectra is strictly related to the extent of tryptophan oxidation; meanwhile an absorbance increase in the 250-260 nm region is characteristic of the formation of a substituted oxindole.

The absorption spectra of oxidized avidin (OXavidin) and HABA-saturated oxidized avidin (OXavidin$_{HABA}$), compared to that of wild type avidin (WTavidin) indicate that the use of HABA to protect the biotin binding sites during oxidation greatly diminishes the rate of tryptophan damage (FIG. 1).

A preferred embodiment of this invention is that of oxidized avidin presenting an UV spectrum wherein the absorbance at 282 and 291 nm does not present the inflexion characteristic of tryptophan residues oxidation with respect to the one observed for WTavidin.

Another preferred embodiment of this invention is that of oxidized avidin presenting an UV spectrum wherein the absorbance at 250-260 nm does not present any increase with respect to the one observed for WTavidin.

Another still preferred embodiment of this invention is that of a method of oxidation of avidin and/or avidin derivatives in the presence of the ligand HABA that prevents tryptophan residues from oxidation.

In strict agreement with the protective effect of HABA, OXavidin$_{HABA}$ shows structural and thermodynamic properties very similar to WTavidin. Thermal stability and conformational changes were determined by circular dichroism spectroscopy before and after oxidation, with and without 4 equivalents of biotin. Melting curves were recorded by following the decrease of dichroic signal at 225 nm in the temperature range 25-95° C. The point of inflection and slope (p) of sigmoidal curves were calculated by means of Boltzman fitting model of the scientific graphing and data analysis Origin® 7.0 software and represent the point of transition through the denatured condition.

For each specific compound, the thermal stability corresponds to the temperature which matches the point of inflection of the corresponding curve registered in the temperature range 25-95° C.

Data (table 1) indicate that oxidation decreases thermal stability, as determined by the decrease in the melting temperature ($T_m$) and by the slope (p) of the sigmoidal curve of OXavidin compared to WTavidin (74.3 versus 79.0° C., and 8.9 versus 14.7, respectively).

Surprisingly, the destabilization effect is almost negligible when the oxidation is performed on HABA-protected avidin as confirmed by the $T_m$ and p values of OXavidin$_{HABA}$ and avidin, 78.1 versus 79.0° C., and 11.2 versus 14.7, respectively.

TABLE 1

|  | Tm (° C.) | p* |
|---|---|---|
| Avidin | 79.0 ± 0.1 | 14.7 ± 0.3 |
| Avidin + 4eq biotin | >95 | n.a. |
| OXavidin | 74.3 ± 0.1 | 8.9 ± 0.1 |
| OXavidin + 4eq biotin | 86.3 ± 0.2 | 20.7 ± 1.1 |
| OXavidin$_{HABA}$ | 78.1 ± 0.3 | 11.2 ± 0.4 |
| OXavidin$_{HABA}$ + 4eq biotin | >95 | n.a. |

*Slope of sigmoidal curve; n.a. = not applicable

Although thermal denaturation is irreversible for both OXavidin$_{HABA}$ and OXavidin when heated without biotin, only OXavidin$_{HABA}$ recovers its secondary structure, similarly to WTavidin, when heated/cooled in presence of biotin (data not shown). These findings confirm that HABA saturation is a very effective way to preserve conformation of avidin subjected to chemical oxidation and explain the consequently retained biotin binding capacity.

A further preferred embodiment of the present invention is that of an oxidized avidin presenting a thermal stability greater or equal to 78° C.

A more preferred embodiment of the present invention is that of an oxidized avidin presenting a thermal stability greater or equal to 78° C. with a slope of the sigmoidal curve greater than 10.

The previous finding is also corroborated by the binding capacity of oxidized avidin (OXavidin$_{HABA}$) to the biotinylated adduct ST2210 which is similar to the one with WT avidin as shown in table 2.

if HABA is added prior to the oxidation (86.3% compared to only 50.9% for the corresponding oxidized avidin in the absence of HABA). A similar result is obtained when the oxidation occurs in the presence of a higher (20 mM) sodium periodate concentration (81.4% versus 49.1%).

A further preferred embodiment of the present invention is that of an oxidized avidin presenting a binding with ST2210 greater or equal to 75% with respect to the 97.4% obtained for WTavidin.

Moreover, tissue permanence of oxidized avidin in mice hind limb, regardless the fact that such oxidation occurred in the presence or not of HABA, is much higher than for WT avidin. This behaviour is strictly correlated to the presence of CHO groups within the glycosylated side-chains of avidin.

In a more preferred embodiment of the present invention, about 8 to 15 CHO residues per avidin (as estimated with 4-amino-3-hydrazino-5-mercapto-1,2,4-triazole or Purpald®'s method) are produced after oxidation with 10 and 20 mM NaIO$_4$.

In an even more preferred embodiment of the present invention, the "HABA-protected" oxidized avidin derivatives (OXavidin$_{HABA}$) maintain a high ST2210 binding capacity and exhibit tissue permanence, at 24 hours and 1 week after injection, that correlate with the number of CHO groups.

Physico-chemical characterisation, by means of Isothermal Titration Calorimetry (ITC), of such avidin's/biotin interaction revealed that ST2210 is able to bind to WTavidin and OXavidin$_{HABA}$ in a comparable manner as demonstrated by

TABLE 2

|  |  | CHO/Avidin | BiotinDOTA | Tissue permanence % ID/100 mg ± SD | |
|---|---|---|---|---|---|
|  | Oxidation conditions | molar ratio ± SD (N) | binding % ± SD (N) | 24 h (N) | 1 week (N) |
| WTavidin | No oxidation | <LoQ (5) | 100@ | 2.4 ± 0.4 (5) | 0.46 ± 0.08 (4) |
| OXavidin | 1 mM NaIO$_4$ | 5.6 ± 0.8 (5) | 77.2 ± 0.9 (4) | 3.1 ± 0.7 (1) | 0.16 ± 0.03 (1) |
|  | 5 mM NaIO$_4$ | 7.5 ± 0.8 (5) | 55.7 ± 2.2 (4) | 6.3 ± 0.3 (1) | 0.99 ± 0.25 (1) |
|  | 10 mM NaIO$_4$ | 8.4 ± 1.0 (6) | 50.9 ± 2.4 (6) | 17.4 ± 2.8 (3) | 9.7 ± 3.2 (3) |
|  | 20 mM NaIO$_4$ | 11.5 ± 1.5* (7) | 49.1 ± 2.1 (6) | 19.1 ± 2.0 (4) | 11.4 ± 1.3 (3) |
|  | 40 mM NaIO$_4$ | 10.9 ± 2.6 (5) | 44.5 ± 0.9 (4) | NT | NT |
| OXavidin$_{HABA}$ | 1 mM NaIO$_4$ + 1 mM HABA | 4.0 ± 0.8 (3) | 99.0 ± 0.2 (3) | NT | NT |
|  | 5 mM NaIO$_4$ + 1 mM HABA | 7.1 ± 1.6 (4) | 95.0 ± 1.7 (3) | NT | NT |
|  | 10 mM NaIO$_4$ + 1 mM HABA | 8.5 ± 1.3 (5) | 86.3 ± 1.6** (3) | 18.4 ± 2.2 (2) | 9.0 ± 1.2 (2) |
|  | 20 mM NaIO$_4$ + 1 mM HABA | 12.9 ± 2.3# (6) | 81.4 ± 1.0#** (4) | 18.5 ± 0.5 (4) | 11.7 ± 2.3 (3) |
|  | 40 mM NaIO$_4$ + 1 mM HABA | 9.8 ± 1.9 (4) | 73.0 ± 0.6 (3) | NT | NT |

N = Number of independent experiments; SD = Standard Deviation; NT = Not Tested
@The experimental value of 97.4 ± 0.5 obtained with biotinDOTA (ST2210) compared to free biotin by HABA assay is assumed as 100% as the reference value for modified avidins;
*p < 0.05 vs 10 mM;
p < 0.01 vs 10 mM (One way Anova followed by Student-Newman-Keuls);
**p < 0.001 vs same without HABA (Two way Anova followed by Bonferroni)

The oxidized avidin obtained according to the optimized method (OXavidin$_{HABA}$) exhibits improved properties compared to oxidized avidin prepared without HABA protection with regard to the binding of ST2210 while maintaining high permanence in the treated tissue (mice muscle limb after i.m. injection). Indeed, when avidin is oxidized with 10 mM of NaIO$_4$, its binding capacity with respect to ST2210, is greater the association constants ($K_A$) and enthalpy change ($\Delta H$) (3.45 versus 2.50×10$^6$ M$^{-1}$, and −1.48 versus −1.71×10$^4$ kcal mol$^{-1}$, respectively). On the contrary, ST2210/OXavidin interaction shows lower $K_A$ (6.45×10$^5$ M$^{-1}$) and higher $\Delta H$ (−0.79×10$^4$ kcal mol$^{-1}$).

According to data of ST2210 binding to oxidized avidins, within experimental error, the determined stoichiometry of interaction is of 3.0, 1.7 and 1.2 molecules of ST2210 per molecule of WTavidin, OXavidin$_{HABA}$ and OXavidin, respectively.

TABLE 3

| | N | $K_A$ $M^{-1}$ | $\Delta H$ kcal mol$^{-1}$ | $\Delta S$ cal mol$^{-1}$ K$^{-1}$ |
|---|---|---|---|---|
| WTavidin | 3.0 ± 0.016 | 3.45E6 ± 3.07E5 | −1.48E4 ± 114.0 | −19.6 |
| OXavidin 20 mM NaIO$_4$ | 1.2 ± 0.012 | 6.45E5 ± 5.69E4 | −0.79E4 ± 117.8 | 0.16 |
| OXavidin$_{HABA}$ 1 mM NaIO$_4$ | 2.5 ± 0.008 | 4.58E6 ± 2.49E5 | −1.29E4 ± 56.2 | −12.7 |
| OXavidin$_{HABA}$ 5 mM NaIO$_4$ | 1.9 ± 0.012 | 5.42E6 ± 5.90E5 | −1.56E4 ± 145.0 | −21.6 |
| OXavidin$_{HABA}$ 10 mM NaIO$_4$ | 1.7 ± 0.008 | 3.34E6 ± 2.12E5 | −1.60E4 ± 109.9 | −23.7 |
| OXavidin$_{HABA}$ 20 mM NaIO$_4$ | 1.5 ± 0.007 | 2.50E6 ± 1.32E5 | −1.71E4 ± 113.7 | −28.0 |

Oxidized avidin, according to the present invention, substantially maintains the biotin binding capacity of the wild type avidin while acquiring the property to interact reversibly with tissue proteins, thus resulting in an ideal candidate for the use in brachytherapy as in the intraoperative avidination for radionuclide treatment IART®.

In a preferred embodiment of the present invention, oxidized avidin is administered in the intraoperative stage, thus generating an "artificial receptor" for the subsequent anticancer agent.

A more preferred embodiment of the present invention is to provide a chemically oxidized avidin to be used as a first brachytherapy agent, endowed with high permanence in treated tissues, in combination with a second agent endowed with affinity for said first oxidized avidin.

An even more preferred embodiment of the present invention is to provide a chemically oxidized avidin to be used as a first brachytherapy agent, endowed with high permanence in treated tissues, in combination with a second anticancer agent endowed with affinity for said first oxidized avidin.

Another embodiment of the present invention is a pharmaceutical composition containing said chemically modified avidin as the first ingredient and a biotinylated therapeutic agent as the second active ingredient.

In one preferred realisation of the invention, the second active ingredient of the above pharmaceutical composition is a biotinylated anticancer agent.

Anticancer agent means an agent capable of fighting tumours. A non-exhaustive list of anticancer agents consists of chemotherapeutic drugs, radiolabelled compounds, effector cells, toxins, cytokines and anticancer cells.

In another preferred realisation of the invention, the therapy will take the form of radiotherapy.

Another preferred embodiment of the present invention consists of the preparation of a kit useful for brachytherapy of breast, muscle, liver, pancreas, bladder, brain, lung, prostate, ovaries, eyes and other organs.

In one preferred realisation of the kit, the two ingredients are in two separate containers.

In a more preferred embodiment, the chemically modified avidin container will consist of an adequate amount of product, formulated in a compatible acidic solution or lyophilized with suitable excipients to form a cake.

In a particularly preferred embodiment, the above mentioned container will take the form of a special syringe suitable for successive administrations of multiple precise volumes into the resection margins or residues of diseased tissue that cannot be removed surgically because of infiltration of vital organs.

Conveniently, the container may also be in a form suitable for the administration of chemically modified avidin as a spray.

Preferably, the various containers, already containing the doses of the individual ingredients, will be made as a single pack bearing the instructions for the modes of administration.

Even more preferably, the various containers have the form of a syringe.

In another particularly preferred embodiment, the kit for use in brachytherapy that, like in TART®, is suitable for sequential locoregional administration of the first ingredient and subsequent systemic or local administration of the second ingredient.

The second ingredient of the composition of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal, rectal means or locally on the diseased tissue.

There are clinical cases where brachytherapy is performed by administering radioisotope directly into the tumour mass (i.e. inoperable brain tumours as described in Julow J., et al., *Prog. Neurol. Surg.*, 2007, 20, 303) or tumour affected organs (i.e. prostate as described in Saito S, et al., *Int. J. Clin. Oncol.*, 2007, 12, 395). In such a case an ideal brachytherapy device would be one showing homogenous distribution and stability within the treated site.

On the basis of experimental data, it has been found that tissue avidination occurs in different tissues like muscle, mammary (shown in the present examples) as well as within brain tissue.

In another still particularly preferred embodiment, the complex oxidized avidin-biotinylated therapeutic agent will be obtained by mixing the two ingredients and subsequently administered to the patient.

The composition of the present invention constitutes a medicine useful for the therapy of operable or not, or not completely removable solid tumours, such as, for example but not exclusively, cancers of the breast, pancreas, lung, pleura, peritoneum, face and neck, bladder, brain, prostate, ovaries, eyes and others organs as described in the patent application WO2004/093916 filed in the name of the Applicant.

According to a preferred embodiment of the invention the oxidized avidin obtained by the process of the invention can be defined as a chemically modified avidin, in which at least one of the mannose residues has been replaced by a residue of the following formula (I)

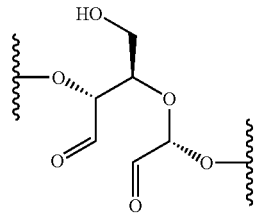 [SMILES: *O[C@H](C=O)O[C@H](CO)[C@H](C=O)O*]

Formula I

A further object of the present invention is pharmaceutical compositions described earlier, in combination with excipients and/or pharmacologically acceptable diluents.

A further embodiment of the invention is a process for the preparation of pharmaceutical compositions characterised by mixing the chemically modified avidin with suitable excipients, stabilizers and/or pharmaceutically acceptable diluents.

An excipient is an inert substance that is added to a drug to provide bulk.

The pharmaceutical composition may also contain a pharmaceutically acceptable carrier, for administration of a therapeutic agent. Such carriers include antibodies and other polypeptides, genes and other therapeutic agents such as liposomes, provided that the carrier may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as lyophilization cakes, tablets, pills, dragees, capsules, liquids, gels, syrups, slurries, suspensions, and the like, for ingestion by the patient.

The subjects to be treated can be animals; in particular, human subjects can be treated.

Dosage treatment may be a single dose schedule or a multiple dose schedule.

The dose will be determined by the expert in the field such as to deliver to the target tissue an amount exerting an effective therapeutic action.

A general dose range could be between 10-100 ml of oxidized avidin solution at a concentration of 3-5 mg/ml. The dose volume will depend on the volume of the target tissue to be treated, i.e. 30 ml for a typical treatment of a breast region surrounding the site of a quadrantectomy (Paganelli G., et al., *The Breast*, 2007, 16, 17) or up to 100 ml for the treatment of a peritoneal cavity.

The biochemical characterization of oxidized avidin includes the estimation of CHO groups by colorimetric reaction with 4-amino-3-hydrazino-5-mercapto-1,2,4-triazole, or Purpald® method known to the expert in field (Avigad G., *Anal. Biochem.*, 1983, 134, 2, 499), using propionaldehyde as a standard.

Panel e, shows $^{111}$In-ST2210 captation after 48 hours from tissue avidination. In the second case scenario ($^{111}$In-ST2210 repeated) the animals received firstly a dose of cold ST2210 and 24 hours later a second dose of $^{111}$In-ST2210.

FIG. 8:

It shows the tissue residence of the WTavidin or OXavidin$_{HABA}$ complexes with ST2210 one week after injection in one hind limb.

FIG. 9:

It shows the brain tissue residence of OXavidin$_{HABA}$ 24 hours after injection through the left side of the skull.

The following examples further illustrate the invention, without limiting it.

EXAMPLES

Example 1

Synthesis and Biochemical Characterization of Oxidized Avidins

The oxidation procedure method comprises the following successive steps:
a) incubating wild type avidin pre-mixed with a molar excess of HABA, with an oxidizing agent such as 10-20 mM sodium periodate in 50-100 mM acetate buffer at pH below 6.0 for 1-5 hours at 4° C. or at room temperature;
b) blocking of the reaction and purification by removal of the oxidizing agent and HABA by chromatography, ultrafiltration, dialysis or other purification methods known to the expert in the field; and
c) lyophilizing or formulating at an acidic pH.

The oxidized avidin was further analyzed for the molecular size by size exclusion chromatography on a biosep-SEC-S3000 column (Phenomenex® chromatography 300×7.8 mm, volume: 14.3 ml) using an isocratic condition with a 100 mM sodium acetate buffer pH 5.5 and 0.15 M NaCl at a flow rate of 1 ml/min at room temperature.

Figure 1:
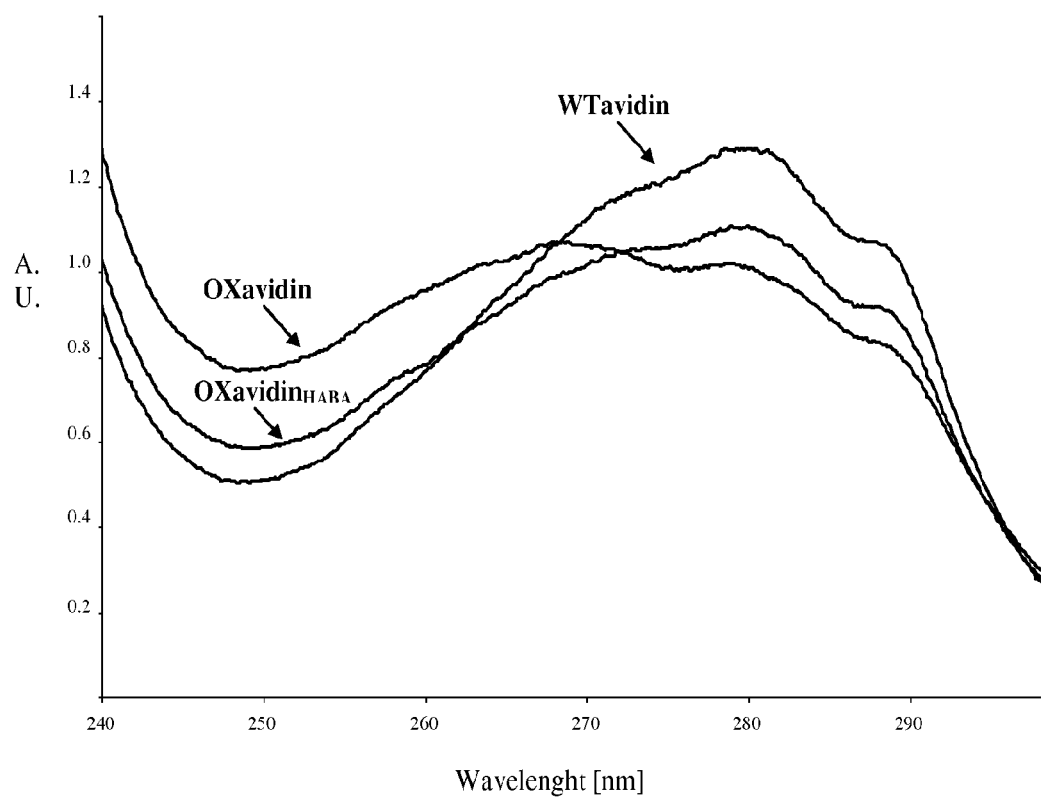
FIG. 1:
It shows the UV spectra of three different forms of avidin.
Figure 2:
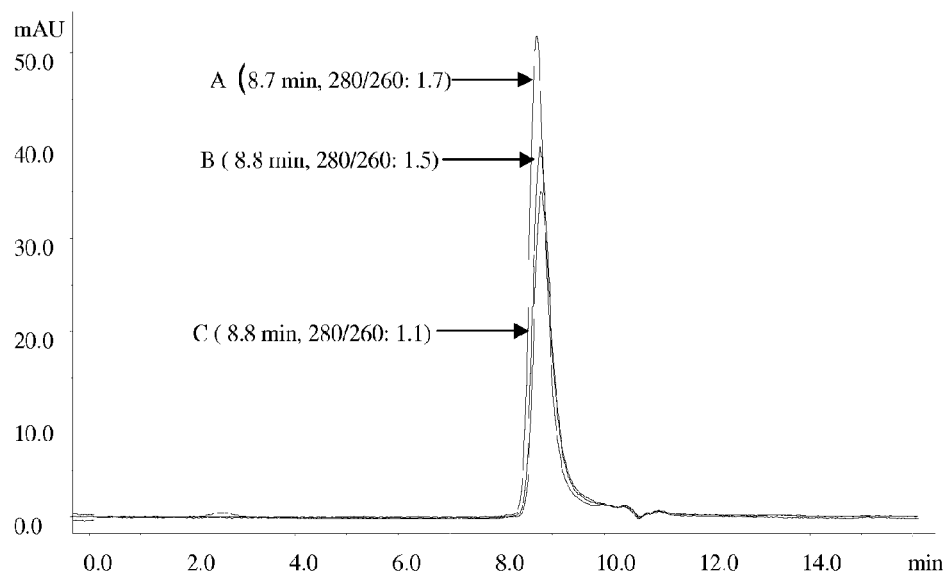
FIG. 2:
The curves A, B and C relate to the elution profiles of WTavidin, OAvidin$_{HABA}$ and Oxavidin respectively on size exclusion chromatography (Biosep-SEC-S3000 size exclusion chromatography column (Phenomenex®, 300×7.8 mm, volume: 14.3 ml) using an isocratic condition with a 100 mM sodium acetate buffer pH 5.5 and 0.15 M NaCl at a flow rate of 1 ml/min at room temperature. The latter two were obtained from WTavidin by oxidation using NaIO$_4$ (20 mM). The ratio 280/260 relates to the integrity of the avidin with respect to the oxidation of tryptophan residues and formation of oxindole.

As shown in FIG. 2 the elution of an oxidized avidin appears slightly delayed compared to native avidin.

Example 2

Biodistribution of Oxidized Avidin in Treated Mice

Oxidized avidin (OXavidin) was evaluated for the permanence in the treated tissue for its biodistribution in not treated organs, as well as for its capacity to capture $^{111}$In-ST2210 in a mouse model simulating intraoperative avidination for radionuclide treatment IART® in comparison to wild type avidin (WTavidin).

The animal model of intraoperative avidination for radionuclide treatment IART® was set up by performing a surgical cut in one hind limb of a mouse, infiltrating radiolabelled avidin in the surgical margins and surrounding tissues and measuring radioactivity in the treated limb at different time points after administration. In a parallel group of mice, the radioactive avidin was infiltrated to the limb without surgery.

The amount of radioactivity, after 1 and 24 hours from administration was similar in the surgically treated and not surgically treated animals. Therefore, further studies were performed by infiltrating avidin without surgery. WTavidin was labelled with $^{125}$I (Perkin Elmer, Italy) according to the Iodo-Gen method (Pierce, Rockford, Ill.). Labelled avidin was separated from free iodine by chromatography on a PD-10 column (Amersham Biosciences, Uppsala, Sweden) and oxidized as previously described in the Example 1 without any prior HABA protection.

ST2210 described in the patent application WO 02/066075 (page 18, 1-[2-[6-[5-[(3aS,4S,6aR)-hexahydro-2-oxo-1H-thieno [3, 4-d]imidazol-4-yl]-1-pentylamino]-1-hexylamino]-2-oxoethyl]-1,4,7,10-tetraazacyclododecane-4,7,10-triacetic acid pentahydrochloride) was labelled with $^{111}$In (Perkin Elmer, Italy) according to a method previously described (Urbano N., et al., *Eur. J. Nucl. Med. Mol. Imaging,* 2007, 34, 68).

Balb/c nu/nu mice (Harlan Udine, Italy) were divided in 8 groups of 5 mice. $^{125}$I-labelled WTavidin or OXavidin were administered intramuscularly (i.m.) in one hind limb of each mouse (400 μg/mouse in 40 μl) and after 1, 24 or 48 hours the mice received intravenously (i.v.) 16 μg of $^{111}$In-ST2210.

Mice were sacrificed 1, 24 or 48 hours after $^{111}$In-ST2210 administration and the treated and controlateral limbs, kidney, liver and blood samples were collected and counted in a gamma-counter (Camberra Packard, Schwadorf, Austria).

Figure 3C:
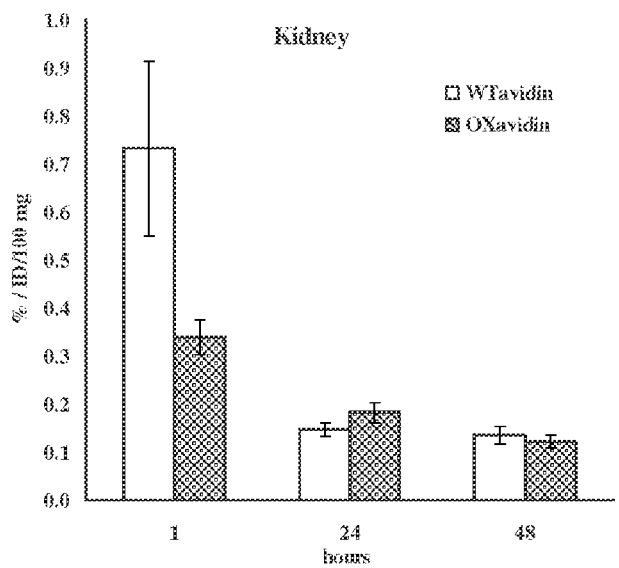
FIG. 3:
It shows the biodistribution of oxidized avidin in treated mice after intramuscular administration. In particular FIG. 3*a* indicates that the amount of oxidized avidin in the treated limb is more than double native avidin after 1 hour from injection. The difference increases with time: native avidin is almost undetectable after 24 and 48 hours, while oxidized avidin represents about 22% and 15% of the injected dose/100 mg of tissue, respectively. The higher concentration of oxidized avidin compared to wild type avidin in the treated limb is, as a consequence, associated to a lower distribution of oxidized avidin and a higher distribution of wild type avidin in the non target organs, particularly in the first hour, as shown for blood, kidney and liver in the FIGS. 3*b*, *c* and *d*, respectively.
FIG. 3*e* shows the distribution of oxidized avidin and wild type avidin in the controlateral limbs.
Figure 3D:
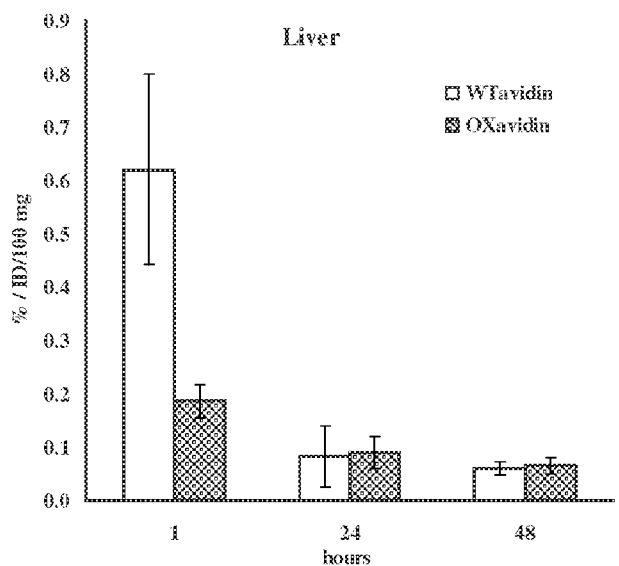
Figure 3E:
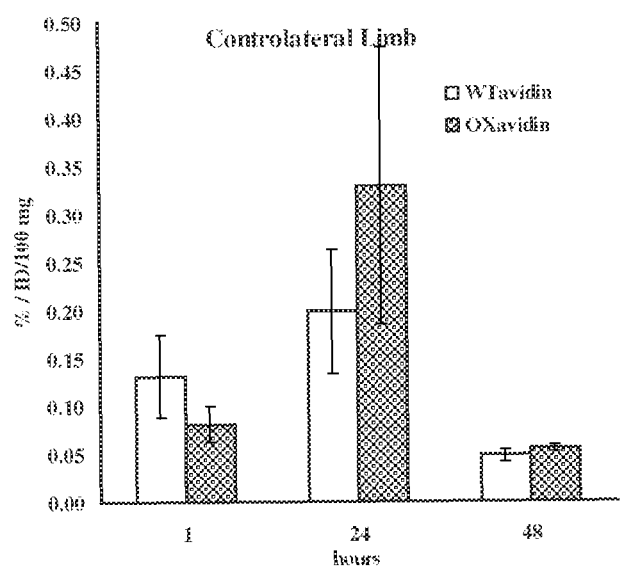

As shown in FIG. 3a the amount of oxidized avidin in the treated limb is more than double the avidin after 1 hour from injection. The difference increases with time: WTavidin is almost undetectable after 24 and 48 hours while OXavidin was about 22% and 15% of the injected dose/100 mg of tissue, respectively. The higher concentration of oxidized avidin compared to wild type avidin in the treated limb was, as a consequence, associated to a lower distribution of oxidized avidin and a higher distribution of wild type avidin in the non target organs, particularly in the first hour, as shown for blood, kidney and liver in the FIGS. 3b, c and d, respectively. FIG. 3e shows the distribution of OXavidin and WTavidin in the controlateral limb.

Since IART®, as described in the patent application WO2004/093916, foresees the local administration of WTavidin (intraoperative injection) followed by the intravenous injection of the anticancer agent after 4-72 hours, it is evident that the use of a chemically modified avidin, as the one in the example of the present invention, offers great advantages.

Example 3

Long Term Tissue Permanence of Wild Type and Oxidized Avidins

Balb/c nu/nu mice (Charles River, Lecco Italy) were injected in one hind limb with 45 μg in 15 μl of either $^{125}$I-labelled WTavidin or $^{125}$I-labelled OXavidin formulated in 100 mM acetate buffer pH 5.5 and at the indicated time points the animals were sacrificed and radioactivity in the treated limb as well as in other non target organs measured by gamma counter (Camberra Packard, Schwadorf Austria).

Figure 4:
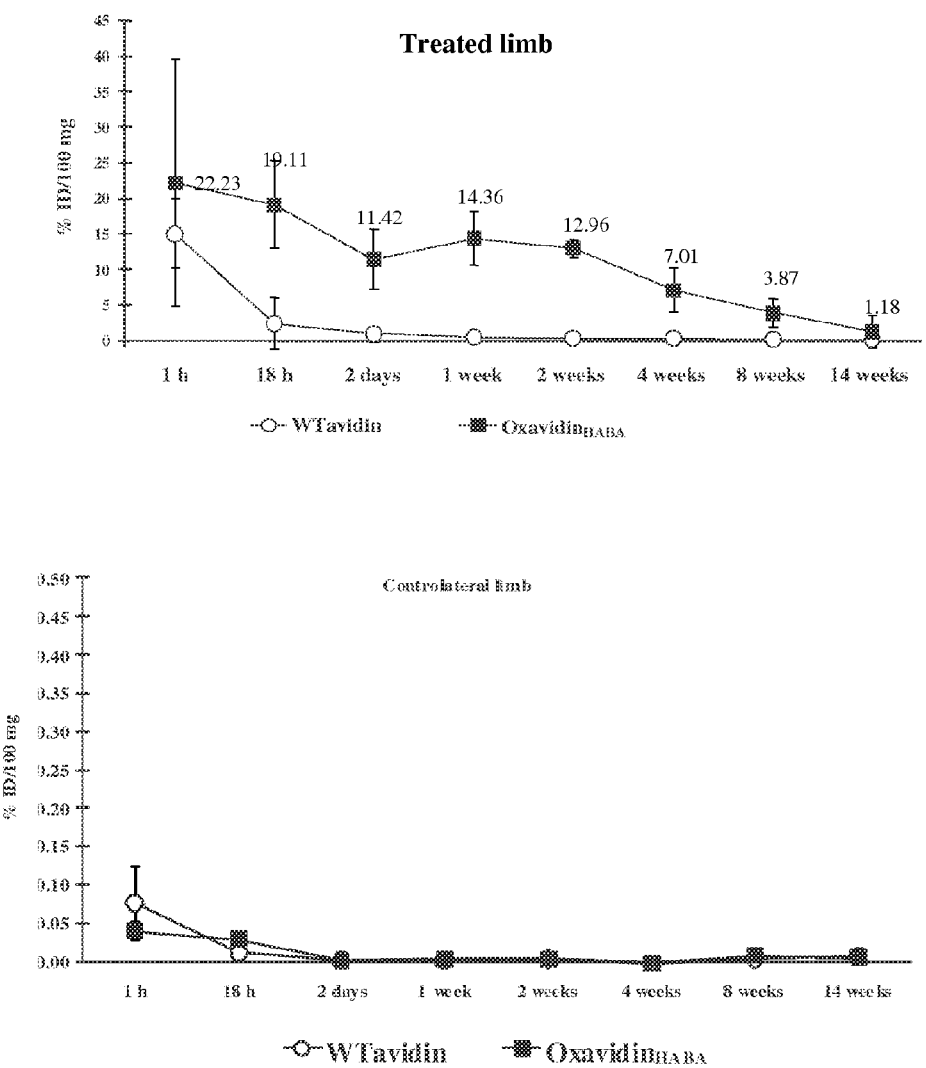
FIG. 4:
It shows the tissue permanence of $^{125}$I-radiolabelled WTavidin and OXavidin$_{HABA}$ in treated and controlateral limbs up to 14 weeks. Such graph indicates that, referred to the 1 hour level, the tissue half life of OXavidin$_{HABA}$ is about 2 weeks as opposed to 2 hours for WTavidin.

The tissue permanence of WTavidin and OXavidin$_{HABA}$ was monitored up to 14 weeks. The tissue half-life of OXavidin, when referred to the 1 hour level, was found to be about 2 weeks as opposed to 2 hours for WTavidin (FIG. 4).

Example 4

Biodistribution of Oxidized Avidin in Mammary Tissue

OXavidin$_{HABA}$ was evaluated for its permanence in the mammary tissue in comparison to WTavidin. 50 μg (in 15 μl) of $^{125}$I-labelled WTavidin or OXavidin$_{HABA}$, prepared according to the general method described in example 1, were administered in the breast region underlying the nipple (3 breasts for each avidin) of rabbits (Francucci Enzo, Rieti, Italy). The animals were sacrificed after 24 h from injection and tissue samples of the injected area of about 200 mg were collected and counted in a gamma counter as previously described. The data are the average (+/−SD) of 3 determinations.

The data in Table 4 show that 8.5 and 65.8% ID of WTavidin and OXavidin$_{HABA}$, respectively are found after 24 hours in the mammary tissue. These data confirm the higher permanence of OXavidin$_{HABA}$, compared to WTavidin, previously observed in the mouse muscular tissue, in the rabbit mammary tissue.

TABLE 4

Permanence at 24 hours of WTavidin and OXavidin$_{HABA}$ in rabbit mammary tissue.
% ID/breast (+/− SD) at 24 h

| WTavidin | OXavidin$_{HABA}$ |
|---|---|
| 8.5 (1.13) | 65.8 (0.08) |

Example 5

Tissue Permanence of Wild Type, Pegylated or Oxidized Avidins

Chemically modified avidins were previously described by other groups with the intent of improving the avidin half-life in circulation (Caliceti P., et al., *J. Control. Release*, 2002, 83, 97; Salmaso S., et al., *Int. J. Pharm.*, 2007, 340, 20). The tissue permanence of WTavidin, PEGavidin prepared according to Caliceti, or OXavidin$_{HABA}$ (oxidized avidin according to the present invention) was evaluated in C57Bl/6 mice (Charles River, Lecco Italy). Animals were injected (i.m.) in one hind limb with 45 µg in 15 µl of $^{125}$I-labelled WTavidin, PEG-avidin or OXavidin$_{HABA}$ formulated in 100 mM acetate buffer pH 5.5. After 24 hours from injection, the animals were sacrificed and radioactivity in the treated limb was measured by gamma counter (Camberra Packard, Schwadorf Austria).

Figure 5:
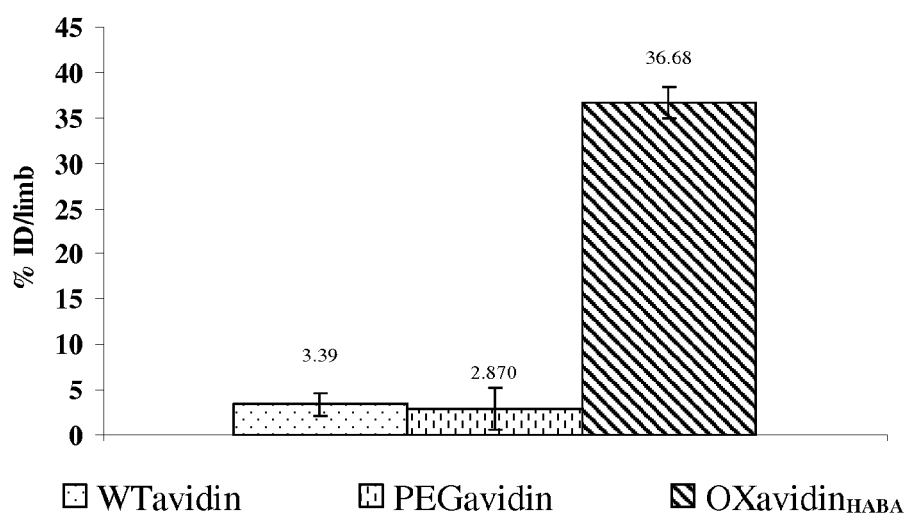
FIG. 5:
It shows the tissue permanence of WTavidin, PEGavidin and OXavidin$_{HABA}$ after 24 hours from injection in one hind limb of Balb/c mice with 45 µg (in 15 µl) of $^{125}$I-labelled WTavidin, PEGavidin or OXavidin formulated in 100 mM acetate buffer pH 5.5. Radioactivity in the treated limb was measured by gamma counter (Camberra Packard, Schwadorf Austria).

PEG-conjugation did not affect the tissue permanence of WTavidin while an increase of tissue permanence was confirmed for the OXavidin$_{HABA}$ (FIG. 5).

Example 6

Tissue localization of WTavidin or OXavidin$_{HABA}$

OXavidin$_{HABA}$ was evaluated for tissue localization in comparison to WTavidin in cryosections of avidinated tissues after intramuscular injection into one hind limb of Balb/c nude mice (Harlan, Udine Italy). The muscles were excised 24 hrs after treatment and serial cryosections were prepared from each sample. Each slide was stained with haematoxylin/eosin to evaluate the tissue morphology or incubated with a mouse anti avidin antibody (A5680, Sigma Aldrich, Italy) followed by anti mouse Alexa fluor 488 (Invitrogen, Milan Italy). Finally, slides were mounted with coverslips and observed under microscope.

Figure 6:
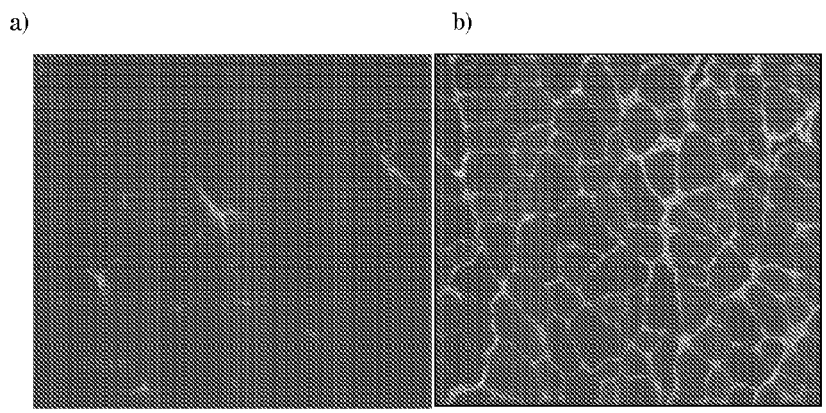
FIG. 6:
It shows sections obtained from Balb/c mice muscles injected with WTavidin (panel a) or OXavidin$_{HABA}$ (panel b) and stained with anti avidin antibody for immunofluorescence: mouse anti avidin ascitic fluid (A5680 batch 064K4826, Sigma Aldrich), followed by Anti mouse Alexa Fluor 488 (batch 99E2.2, Molecular Probes). Panel a shows a weak dotted localization while sections from muscles injected with OXavidin$_{HABA}$ show a strong homogenous distribution. In both cases avidin was localized at the interstitium.

As shown in the FIG. 6, sections obtained from muscles injected with WTavidin (panel a) show a weak dotted localization while sections from muscles injected with OXavidin$_{HABA}$ (panel b) show a strong homogenous distribution. In both cases avidin was localized at the interstitium. Haematoxylin/eosin staining showed no histological abnormalities of muscle after 24 hrs from injection with either WTavidin or OXavidin$_{HABA}$ (data not shown).

Example 7

$^{111}$In-ST2210 Single and Repeated Captation

Oxavidin$_{HABA}$ was evaluated for its capacity to capture $^{111}$In-ST2210 in a mouse model simulating intraoperative avidination for radionuclide treatment IART® in comparison with WTavidin.

Balb/c nu/nu mice (Harlan Udine, Italy) were injected (i.m.) in one hind limb with 45 µg in 15 µl of either WTavidin or Oxavidin$_{HABA}$ formulated in 100 mM acetate buffer pH 5.5. After 48 hours from injection, the animals received intravenously (i.v.) 5 µg of $^{111}$In-ST2210.

Groups of 5 animals were sacrificed at the indicated time points and radioactivity in the treated limb as well as in other non target organs measured by gamma counter (Camberra Packard, Schwadorf Austria).

Figure 7:
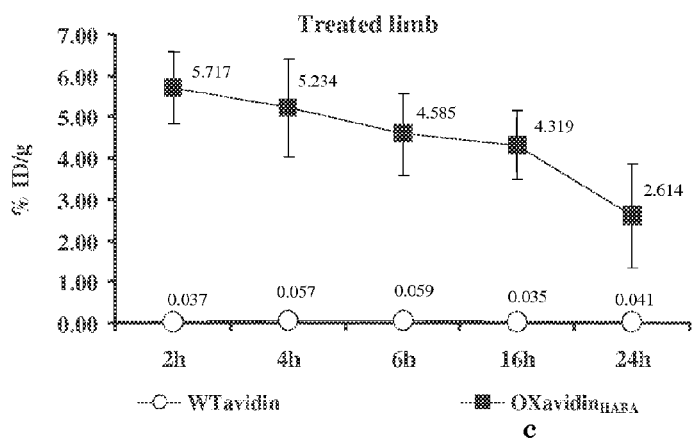
FIG. 7:
It shows the permanence at various time points of i.v. injected [111]In-ST2210 in Balb/c mice hind limb which were treated 48 hours before with WTavidin or OXavidin$_{HABA}$ (panel a). Panels b, c and d refer to $^{111}$In-ST2210 captation in liver, kidney and spleen, respectively, after i.v. injection of $^{111}$In-ST2210.
Figure 7:
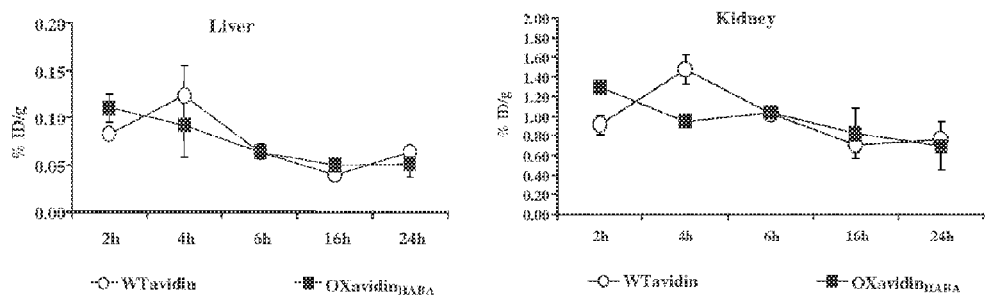

As shown in FIG. 7a the specific captation of $^{111}$In-ST2210 after 2 hours from i.v. injection is much higher for the OXavidin$_{HABA}$ treated tissue than for the WTavidin treated one. These differences in the radioactivity permanence persist at the subsequent time points up to 24 hours from $^{111}$In-ST2210 i.v. administration, thus confirming the long lasting tissue avidination obtained with OXavidin$_{HABA}$. The distribution of $^{111}$In-ST2210 in non target organs is similar for WTavidin and OXavidin$_{HABA}$ (FIGS. 7 b,c,d).

One group of animals received a first intravenous dose of 5 µg of cold ST2210 24 hours prior to a second one of 5 µg $^{111}$In-ST2210. The former occurred 24 hours after avidination. The animals were sacrificed 2 hours after i.v. injection of radiolabelled-ST2210 and radioactivity in the treated limb was measured by gamma counter as above.

As shown in FIG. 7e the second dose of $^{111}$In-ST2210 was captured by the Oxavidin$_{HABA}$-treated limb at a level comparable to that obtained with the single dose. This result suggests that the avidinated tissue was not saturated by the single dose of ST2210 used in this study and that fractionation of a given intended dose is feasible.

Example 8

$^{111}$In/$^{90}$Y-ST2210 Captation and Therapeutic Efficacy in NeuT Transgenic Mice Balb/c transgenic mice carrying the activated rat HER-2/neu oncogene (Balb-NeuT mice (Di Carlo E., et al., Lab. Invest., 1999, 79, 10, 1261) were kindly provided by Prof Guido Formi, University of Turin Italy. Four animals/group were injected intranipple in both IV° breasts with 25 µl (3.3 mg/ml) of either vehicle, WTavidin or OXavidin$_{HABA}$ at week 12 of life that corresponds to the period in which the animals develop carcinoma in situ in all 10 breasts. After 48 hours the animals received a dose (i.v.) of 4.4 µg of radiolabelled ST2210. This dose corresponded to 800 µCi of $^{90}$Y for therapeutic purposes with a spike of 40 µCi of $^{111}$In-ST2210 for dosimetric purposes. Two animals/group were sacrificed 3 hours after administration and both breasts IV and III excised and counted in a gamma counter as above. Non target organs were also collected weighted and counted. Data are expressed as the % ID/g of tissue. The effect of this pre-targeted brachytherapy on the tumoral lesions were evaluated by whole mount analysis of the mammary gland as described previously (De Giovanni C., et al., Cancer Research, 2004, 64, 4001).

Data shown in Table 5 indicate that specific capitation of radiolabelled ST2210 is evident in the IV breast OXavidin$_{HABA}$-treated but neither in IV breast of WTavidin nor in vehicle-treated breast of NeuT mice. The breasts III from all animal groups are negative (blood background level) indicating that avidination is confined to the treated breast. The data on the overall are in agreement with the difference in tissue permanence previously described for WTavidin and OXavidn$_{HABA}$. The background radioactivity in blood and non-target organs including kidney, liver and spleen was below 0.2% ID/g of tissue in any case thus indicating no need to perform a chase step with biotinylated albumin as needed in the current version of intraoperative avidination for radionuclide treatment IART®. The effect of the present OXavidin$_{HABA}$-based brachytherapy on the mammary gland of NeuT mice resulted in a significant reduction of cancer lesions in OXavidin$_{HABA}$-treated breasts compared to vehicle or p WTavidin-treated breast (data not shown).

TABLE 5

| | NeuT model % ID of $^{111}$In/$^{90}$Y-ST2210/g (±SD) | | | | | |
|---|---|---|---|---|---|---|
| | Blood | Spleen | Kidney | Liver | Breast IV | Breast III |
| Vehicle | 0.003 (0.001) | 0.007 (0.002) | 0.143 (0.018) | 0.023 (0.001) | 0.007 (0.002) | 0.005 (0.001) |
| WTavidin | 0.002 (0.001) | 0.008 (0.001) | 0.161 (0.035) | 0.027 (0.006) | 0.028 (0.027) | 0.007 (0.002) |
| OXavidin$_{HABA}$ | 0.003 (0.001) | 0.006 (0.001) | 0.101 (0.008) | 0.019 (0.003) | 1.784 (0.512) | 0.008 (0.001) |

Example 9

One Step Brachytherapy $^{125}$I-OXavidin$_{HABA}$ was saturated in vitro with ST2210, purified from unbound ST2210 by ultrafiltration and intramuscularly injected into one hind limb of Balb/c mice. The same protocol was followed with regard to WTavidin.

The amount of WTavidin or OXavidin$_{HABA}$ saturated with ST2210 in the treated limb, was compared to free WTavidin or OXavidin$_{HABA}$ after 1 week.

Results in FIG. 8 indicate that meanwhile OXavidin$_{HABA}$ either complexed or not with ST2210 was still present a week after injection (17% ID/100 mg), WTavidin almost completely disappeared (<0.5% ID/100 mg) thus providing evidence that OXavidin$_{HABA}$ pre-saturated with a biotinylated agent behaves the same as free OXavidin$_{HABA}$ and it could be used for one step brachytherapy.

Example 10

Figure 9:
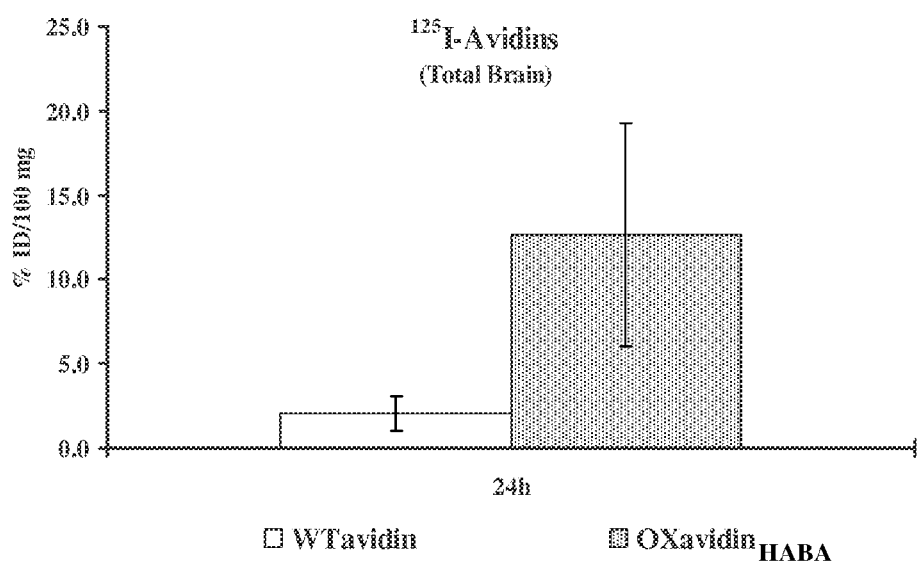

Brain Permanence of Oxavidin$_{HABA}$ Compared to WTavidin $^{125}$I-WTavidin or OXavidin$_{HABA}$, prepared as previously described, were injected in a 5 μl volume (16 μg dose) into the brain of Balb/c mice under general anaesthesia. The injection into brain was performed through the left side of the skull, by using a Hamilton syringe, at a depth of 4-5 mm. Results in FIG. 9 indicate that similarly to muscle and breast, the residence of OXavidin$_{HABA}$ in the brain, after 24 hours from injection, is about 12.65±6.59% ID/100 mg of tissue. The amount of WTavidin as in other tissues previously evaluated, is less than 2.08±1.03% ID/100 mg of tissue. This result indicates that OXavidin$_{HABA}$ could be useful for brachytherapy of brain tumors or for targeting to the brain biotinylated therapeutics.

The invention claimed is:

1. An oxidized avidin in which at least one mannose residue per avidin molecule is replaced by a residue of the following formula

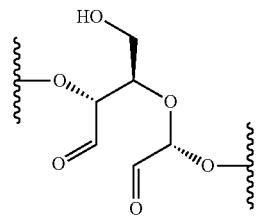

wherein said oxidized avidin contains about 8 to 15 aldehyde moieties and has a thermal stability equal to or greater than 78° C.

2. A complex consisting of the oxidized avidin according to claim 1 and a biotinylated therapeutic agent.

3. The complex according to claim 2, wherein the biotinylated therapeutic agent is an anticancer agent.

4. A pharmaceutical composition comprising an oxidized avidin in which at least one mannose residue per avidin molecule is replaced by a residue of the following formula

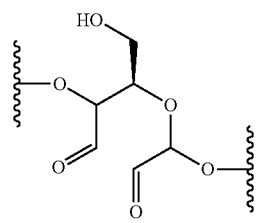 [SMILES: *OC(C=O)O[C@H](CO)C(C=O)O*]

wherein said oxidized avidin contains about 8 to 15 aldehyde moieties and has a thermal stability equal to or greater than 78° C. or the complex according to claim 2 with a pharmaceutically acceptable excipient thereof.

5. A kit comprising the pharmaceutical composition according to claim 4 containing the oxidized avidin in a first container and the biotinylated therapeutic agent in a second container.

6. The kit according to claim 5 for a two-step adjuvant intra- and perioperative locoregional and/or systemic therapy, wherein the two containers have the form of a syringe.

* * * * *

UNITED STATES PATENT AND TRADEMARK OFFICE
CERTIFICATE OF CORRECTION

PATENT NO.        : 8,562,947 B2                                   Page 1 of 1
APPLICATION NO.   : 12/670925
DATED             : October 22, 2013
INVENTOR(S)       : De Santis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 593 days.

Signed and Sealed this

Fifteenth Day of September, 2015

Michelle K. Lee
*Director of the United States Patent and Trademark Office*